US00PP19341P2

(12) United States Plant Patent
Lyrene

(10) Patent No.: US PP19,341 P2
(45) Date of Patent: Oct. 14, 2008

(54) SOUTHERN HIGHBUSH BLUEBERRY PLANT NAMED 'FARTHING'

(50) Latin Name: *Vaccinium corymbosum L.*
Varietal Denomination: Farthing

(75) Inventor: Paul M. Lyrene, Micanopy, FL (US)

(73) Assignee: The University of Florida Board of Trustees, Gainesville, FL (US)

( * ) Notice: Subject to any disclaimer, the term of this patent is extended or adjusted under 35 U.S.C. 154(b) by 0 days.

(21) Appl. No.: 11/906,298

(22) Filed: Oct. 1, 2007

(51) Int. Cl.
*A01H 5/00* (2006.01)

(52) U.S. Cl. ..... Plt./157

(58) Field of Classification Search ..... Plt./157
See application file for complete search history.

*Primary Examiner*—Annette H Para
*Assistant Examiner*—S. B. McCormick-Ewoldt
(74) *Attorney, Agent, or Firm*—Jondle & Associates, P.C.

(57) ABSTRACT

A southern highbush blueberry (*Vaccinium corymbosum*) cultivar particularly distinguished by having a low chilling requirements (300 hours below 7° C.) with prolific early-spring leafing, a vigorous, dense bush with numerous canes, dark green leaves and good survival in the field, early ripening (50% ripe berries in north Florida by May 5) and a high yield of berries that are sweet and firm with a small, dry picking scar.

4 Drawing Sheets

Genus and species: *Vaccinium corymbosoum* L.
Variety Denomination: 'Farthing'.

BACKGROUND OF THE NEW PLANT

The invention relates to a new and distinct variety of southern highbush blueberry (*Vaccinium corymbosum* L.) hybrid plant named 'Farthing.' 'Farthing' is intended for production of fresh-market blueberries in early spring from areas with mild winters and early spring warmth. 'Farthing' is a southern highblush blueberry clone distinguished by its low chilling requirement, its vigorous, disease-resistant bush and by its very firm sweet berries that ripen from late April through mid-May when grown in north Florida. Several thousand plants of 'Farthing' have been propagated by softwood cuttings at Gainesville, Fla. and the resulting plants have all been phenotypically indistinguishable from the original plant.

'Farthing' originated as a seedling from the cross of the proprietary female parent, 'FL 96-27' (unpatented) with the male parent, 'Windsor' (U.S. Plant Pat. No. 12,783) and was made as part of the University of Florida breeding program in a greenhouse at Gainesville, Fla. in February, 1996. The seedling was first fruited in a high-density field nursery in the spring of 1998. After the third year of fruiting in the field, in the spring of 2000, 'Farthing' was propagated by softwood cuttings in June, 2000, and a 20-plant test plot was established as part of a variety test in a commercial field at Windsor, Fla. in January, 2001. Based on the growth and yield of this plot, 'Farthing' was re-propagated by softwood cuttings in June 2002, and test plots were planted the following winter on blueberry farms in north Florida at Archer (500 plants), Waldo (500 plants), and Windsor (100 plants). These plots were observed carefully from flowering through fruit ripening each year, and no mutations or off-type plants have been observed. The present invention has been found to retain its distinctive characteristics through successive asexual propagations.

SUMMARY OF THE INVENTION

The following are the most outstanding and distinguishing characteristics of this new cultivar when grown under normal horticultural practices in Florida.

1. A low chilling requirement with prolific early-spring leafing;
2. A vigorous, dense bush with numerous canes and dark green leaves;
3. Early ripening (50% ripe berries north Florida by May 5 and about 6 days later than 'Star'); and
4. Berries that are sweet and firm with a small, dry picking scar.

DESCRIPTION OF THE PHOTOGRAPHS

The color chart used in this specification is "The Pantone Book of Color", by Leatrice Eiseman and Lawrence Herbert. (1990). Harry N. Abrams, Inc., Publishers, N.Y. Where colors in the drawings differ from the Pantone color designations in the descriptions, the Pantone color designations are accurate. The colors shown are as true as can be reasonably obtained by conventional photographic procedures.

FIG. 1 shows a row of 'Farthing' plants in late April in north Florida. The row was established 4 and one-half years earlier using small rooted cuttings. The dense canopy, dark-green leaves, and the presentation of the berries on the outer surface of the bush are visible.

DESCRIPTION OF THE NEW CULTIVAR

Figure 1:
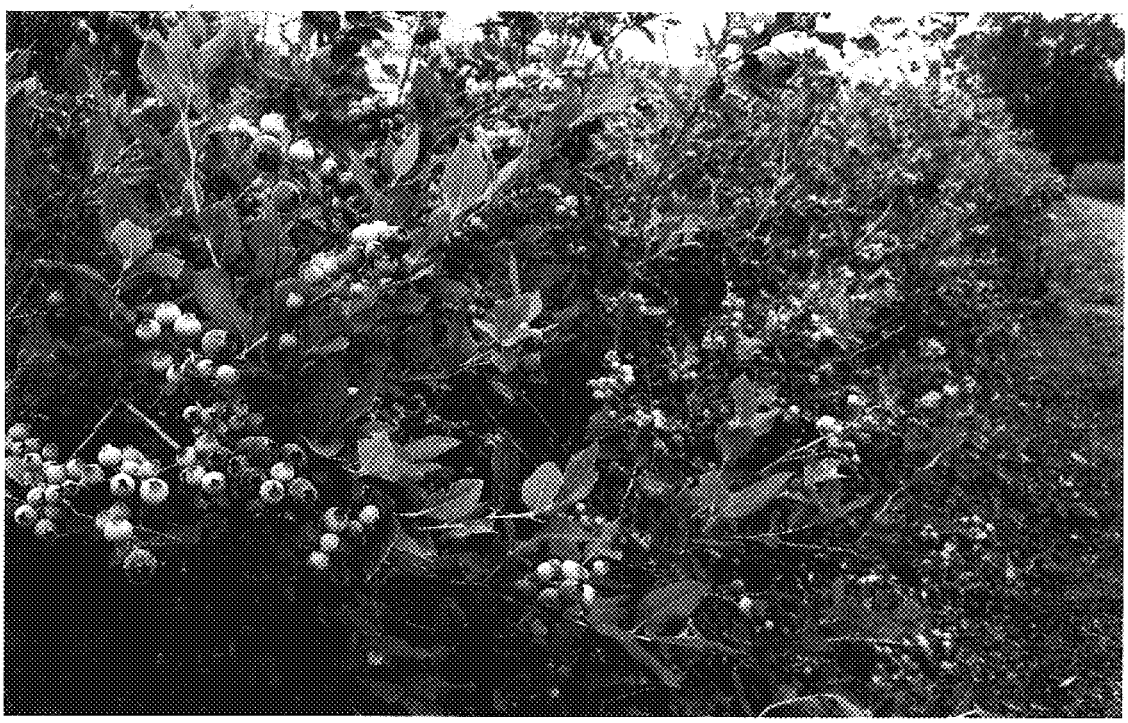
Figure 2:
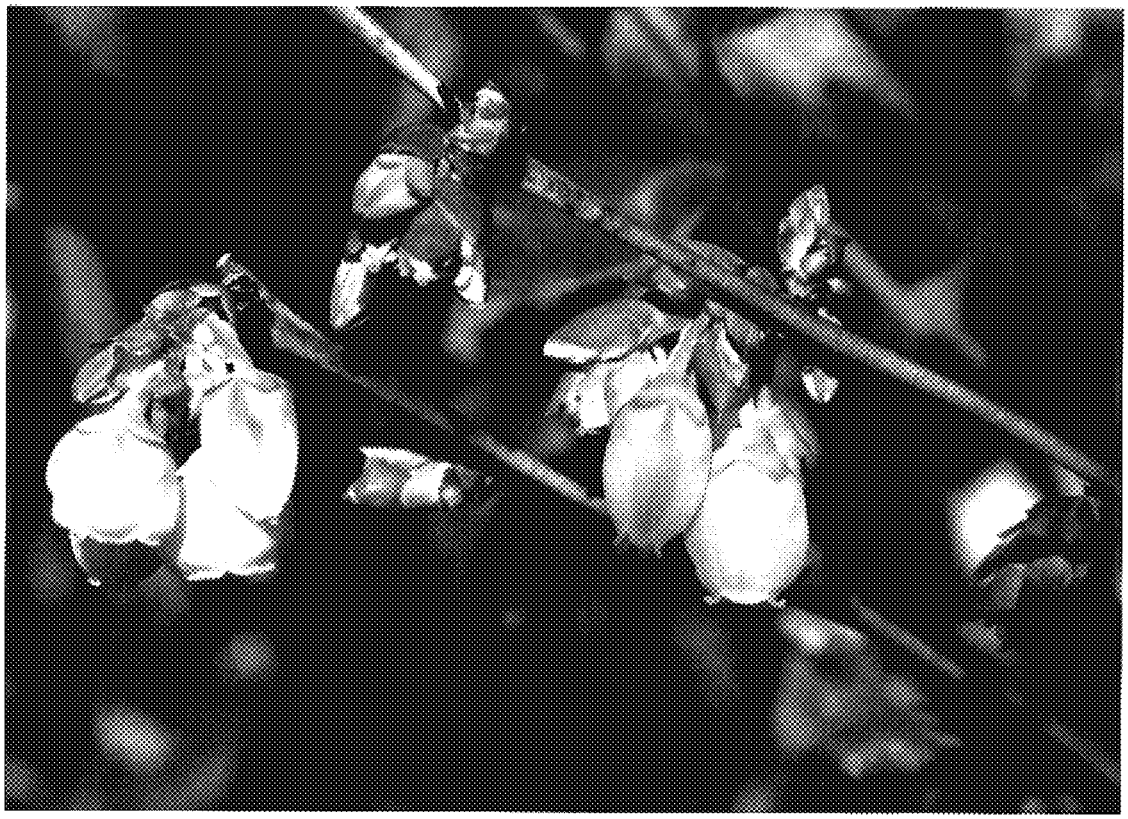
FIG. 2 shows several clusters of opening flowers during the early stages of flowering in February. The flowers are pink in color here but are more nearly white if the weather is warmer during flowering, and the pink fades to white as the flowers become more mature.
Figure 3:
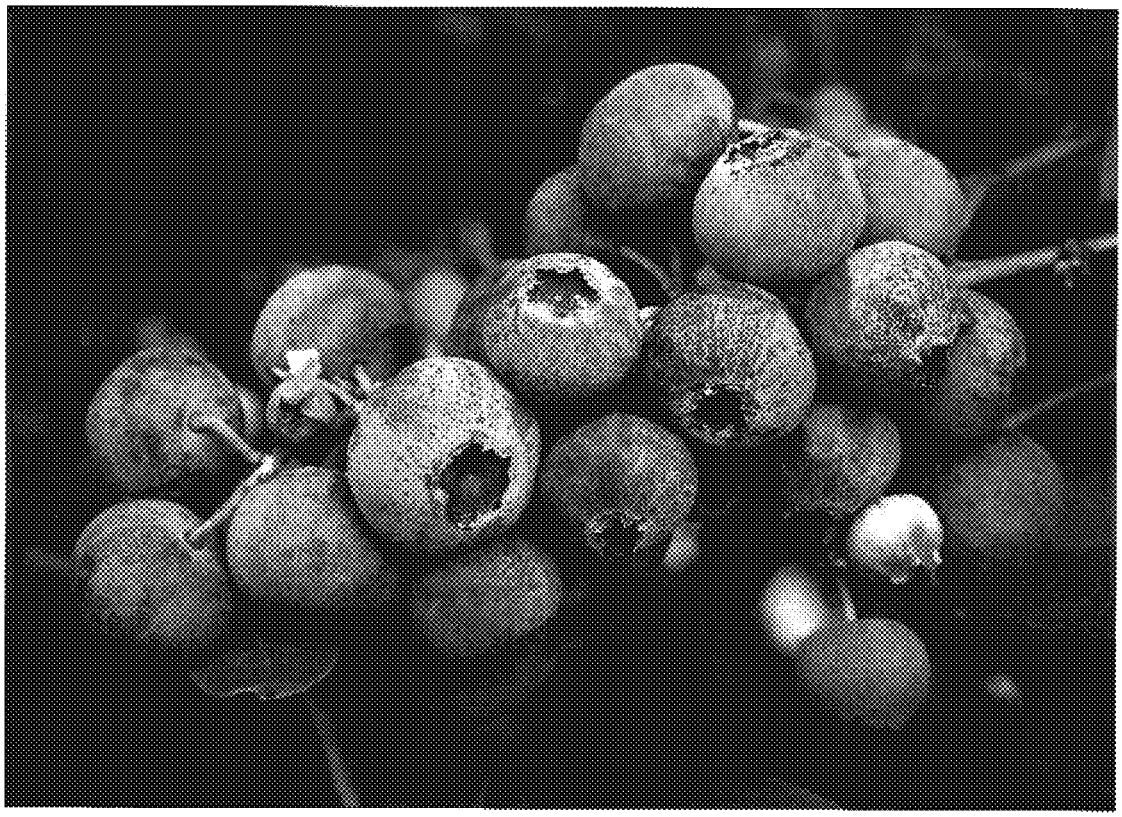
FIG. 3 shows several clusters of berries ripening in the field. The freckling pattern is due to naturally occurring minerals in the water being used in overhead irrigation of the plants and is not an inherent feature of the berries.
Figure 4:
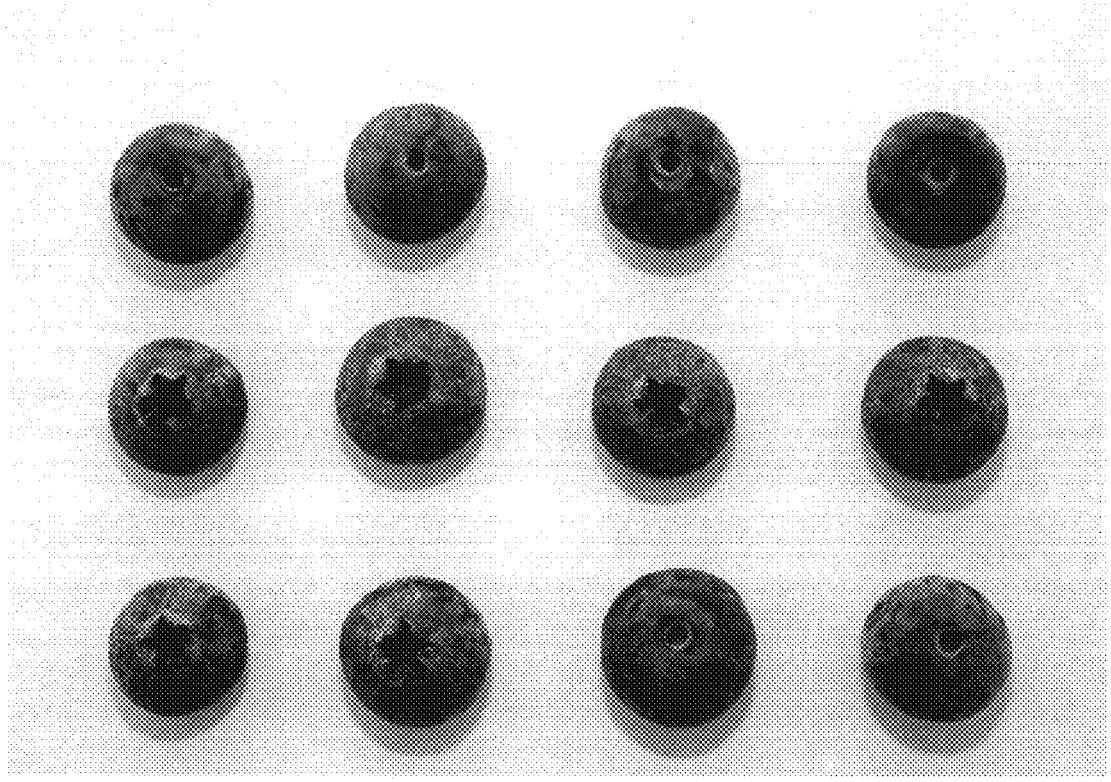
FIG. 4 shows both the upper and lower surfaces of representative berries at close range. The small, dry picking scars and the five-printed star formed by the calyx lobes on some of the berries are visible.

The following detailed description sets forth the distinctive characteristics of 'Farthing'. The data which define these characteristics were collected from asexual reproductions carried out in Florida. The plant history was taken on 4- and one-half year-old plants. The following descriptions relate to plants grown in the field in north Florida (Windsor, Fla.). Color designations are from "The Pantone Book of Color" (by Leatrice Eiseman and Lawrence Herbert; Harry N. Abrams, Inc., Publishers, New York, 1990). Where the Pantone color designations differ from the colors in the Drawings, the Pantone colors are accurate.

DETAILED BOTANICAL DESCRIPTION

Classification:

*Family.*—Ericaceae.

*Botanical.*—*Vaccinium corymbosum* L.

*Common name.*—Southern Highbush Blueberry.

Parentage:

*Female parent.*—'FL 96-27', a proprietary southern highbush blueberry plant (unpatented).

*Male parent.*—'Windsor' (U.S. Plant Pat. No. 12,783).

Market Class: 'Farthing' produces southern highbush blueberries suitable for both the fresh and processed fruit markets.

Plant:

*General.*—Bush characteristics were taken from a plot of one-hundred 4- and one-half year-old plants growing in a test plot in a commercial field near Windsor in northeast Florida.

*Plant height.*—2.3 m.

*Canopy* (*diameter measured at widest part of the bush*).—2.2 m.

*Plant vigor.*—High; more vigorous than 'Star'.

*Growth habit.*—Between upright and spreading; produces a dense canopy.

*Flower bud density* (*number*) *along flowering twigs in January.*—Very high.

*Twigginess.*—Medium to high.

*Tendency toward evergreenness.*—Medium to high.

*Productivity.*—In northeast Florida. 'Farthing' produces 5 to 10 pounds of berries per bush on plants 3 years old or older.

*Chilling requirement.*—300 hours below 7° C.

*Cold hardiness.*—Flowers and fruit are hardy to −3° C.; the plant is hardy to −15° C. during winter dormancy.

*Ease of propagation.*—'Farthing' is easy to propagate from softwood cuttings; the plants survive and grow well in nursery beds.

Trunk and Branches:

*Suckering tendency.*—Medium; four-year-old plants have an average of 10 major canes rising from a crown 30 cm in diameter.

*Surface texture* (*of strong, 6-month-old shoots observed in August*).—Smooth.

*Surface texture* (*of strong, 1-year-old wood observed in August*).—Becoming rough through formation of vertical cracks in the bark due to stem thickening.

*Surface texture* (of 3-*year-old and older wood*). Rough due to exfoliation and production of vertical cracks.

*Color of 6-month-old twigs observed in August in the field.*—"Pale Star", Pantone 12-0626.

*Color of 1-year-old, rough bark observed in August.*—"Moonlight" , Pantone 15-1309.

*Color of 3-year-old rough-textured canes.*—"Moonlight", Pantone 15-1309.

*Internode length on strong, upright shoot measured in August.*—Average 1.3 cm.

Leaves:

*Length, means* (*including petiole, from tip of petiole to end of blade*).—5.8 cm Width, mean (at widest point): 2.7 cm.

*Shape.*—Ovate, terminating in a very short dew tip, 0.03 cm long, which is visible with a 15X microscope.

*Margin.*—Minutely serrate; the margin is slightly revolute along the petiolar half of the leaf blades.

*Color.*—Upper surface: "Black Forest", Pantone 19-0315. Lower surface: "Mistletoe", Pantone 16-0220.

*Pubescence on both surfaces.*—Absent.

*Pubescence on margins.*—Absent.

*Relative time of leafing versus flowering.*—In commercial fields in North Florida, where the bushes are sprayed with hydrogen cyanomide in midwinter, 'Farthing' begins to produce new leaves at the time of full bloom.

Flowers:

*Arrangement.*—Flowers are arranged alternately along a short, leafless, deciduous branch.

*Fragrance.*—Little or none.

*Shape.*—Urceolate.

*Flowering period.*—Mean date of 50% open flowers in Windsor, Fla. is February 8; averages 3 days before 'Star'.

*Cluster* (*tight, medium, loose*).—Medium.

*Average number of flowers per cluster.*—6 to 7.

*Petals.*—Fused into a corolla with 5 lobes.

*Pedicel.*—Length at time of anthesis: 0.5 cm to 0.6 cm. Color: "Moonlight Mauve", Pantone 16-2614.

*Peduncle.*—Length at time of anthesis: Highly variable; median is 0.7 cm Color: "Raspberry Rose", Pantone 18-2333; rose coloration is less intense in shade or for flowers developing under warm temperatures.

*Calyx.*—Cup diameter at anthesis tip of lobe of tip of opposite lobe): 0.6 cm to 0.7 cm. Surface texture: Smooth. Color at anthesis: "Chalk Pink", Pantone 13-1904, but can vary to "Conch Shell", Pantone 15-1624, in cold weather and bright sunshine.

*Corolla.*—Length of tube: Medium is 0.8 cm. Diameter of tube (at widest point): 0.8 cm. Aperture diameter: 0.2 cm to 0.3 cm. Surface texture: Smooth. Color at anthesis: White to "Pearl Blush", Pantone 12-1207; the more pink shades are characteristics of flowers before opening and flowers that are developing in cold weather. Length (from pedicel attachment point to corolla tip excluding the pedicel): 0.9 cm.

Reproductive Organs:

*Style length* (*top of ovary to stigma tip*).—0.8 cm to 0.9 cm.

*Location of tip of stigma relative to lip of the corolla.*—Stigma tip is about even with the outer edge of the corolla tube.

*Pollen.*—General: The pollen includes some tetrads in which one or two spores have aborted. Although pollen staining appears to be slightly below normal, pollen fertility is not expected to be a problem in commercial fields. Abundance of shed: Very high. Staining with 2% acetocarmine (a measure of potential pollen fertility): 99%. Color of dried pollen: "White Swan", Pantone 12-0000.

Self Fruitfulness: Higher than for most southern highbush blueberry cultivars from Florida. In one greenhouse test, 79 berries were harvested from 87 flowers after manual self-pollination. However, planting in field configurations that promote cross pollination with other southern highbush clones is recommended for all southern highbush in Florida.

Fruit:

*Mean date of first commercial harvest (25% of berries ripe).*—April 20.

*Mean date of mid-harvest.*—May 4.

*Mean date of last harvest.*—May 20.

*Diameter of calyx aperture on mature berry.*—0.7 cm.

*Size and shape of calyx lobes on mature berry.*—Medium to well-developed; 5-pointed star formed by calyx lobes.

*Depth of corolla dish.*—0.2 cm.

*Pedicel length on ripe berry.*—0.7 cm to 0.8 cm.

*Peduncle length on ripe berry.*—Variable; 0.9 cm to 1.0 cm.

*Detachment force for ripe berries.*—Medium.

*Number of berries per cluster.*—4.

Berry:

*Cluster (tight, medium, or loose).*—Medium.

*Weight (on well-pruned plants).*—2.1 g per berry compared to 1.8 g per berry for 'Star'.

*Height.*—1.27 cm.

*Width.*—1.71 cm.

*Shape.*—Subglobose; polar diameter shorter than equatorial diameter.

*Surface color of mature berries while on the plant.*—"Limestone", Pantone 16-4702.

*Surface color of the berries after harvesting and packing.*—"Charcoal Gray", Pantone 18-0601.

*Surface color of ripe berry after polishing.*—"Shale", Pantone 19-3903.

*Internal flesh color of ripe berry.*—"Celery Green", Pantone 13-0532.

*Surface wax.*—Medium in amount and in persistence during handling of the berry.

*Pedicel scar.*—Small and dry.

*Firmness.*—High.

*Flavor.*—Sweet, subacid.

*Texture.*—Good; small seeds, very juicy and thin skinned.

Seeds:

*Color of dried seeds.*—"Tobacco Brown", Pantone 17-1327.

*Weight of well-developed dried seed.*—0.38 mg per seed.

*Length of well-developed dried seed.*—0.22 cm.

*Width of well-developed dried seed.*—0.12 cm.

Resistance to Diseases, Insects and Mites: 'Farthing' has grown vigorously and shows good bush survival in the field. 'Farthing' appears to have above-average resistance to root rot (*Phytophthora cinnamomi*) and stem blight (*Botryosphaeria dothidia*). 'Farthing' has shown no signs of cane canker (*Botryosphaeria corticis*) susceptibility in the field. The fungal leaf spots that are common on highbush blueberries grown in Florida are easily controlled by approved fungicides. In the absence of fungicide applications, 'Farthing' leaves appear to have better leaf-spot resistance than most other Florida southern highbush blueberry cultivars.

COMPARISON WITH PARENTAL AND KNOWN CULTIVARS

'Farthing' differs from the proprietary female (seed) parent 'FL 96-27' (unpatented) in that 'Farthing' has a larger berry and higher anthocyanin development as manifested by the usually black (as opposed to red) skin color beneath the epicuticular wax of the ripe berry than 'FL 96-27'. Additionally, 'Farthing' produces new leaves more prolifically shortly after flowering than 'FL 96-27'.

'Farthing' differs from the male (pollen) parent 'Windsor' (U.S. Plant Pat. No. 12,783) in that 'Farthing' is somewhat lower in chilling requirements and flowers somewhat earlier than 'Windsor'. Additionally, 'Farthing' has a small, dry scar, while 'Windsor' has a large scar that causes problems in packing and shipping.

'Farthing' differs from the commercial variety 'Star' (U.S. Plant Pat. No. 10,675), an important variety widely planted in Florida and Georgia for early-season blueberry production. 'Farthing' is more vigorous and has a higher yield potential than 'Star' and is resistant to cane canker disease (caused by *Botryosphaeria corticis*), to which 'Star' is susceptible.

'Farthing' differs from the commercial variety 'Abundance' (U.S. Plant Pat. No. 16,476) in that 'Farthing' has ovate leaves that are shorter (5.8 cm) and narrower (2.7 cm) than the oval leaves of 'Abundance' which are longer (6.6 cm) and wider (3.3 cm).

I claim:

1. A new and distinct cultivar of southern highbush blueberry plant as shown and described herein.

* * * * *